(12) United States Patent
Cherniak et al.

(10) Patent No.: US 10,112,970 B2
(45) Date of Patent: Oct. 30, 2018

(54) PROCESS FOR THE PREPARATION OF 17-DESOXY-CORTICOSTEROIDS

(71) Applicant: Taro Pharmaceutical Industries Ltd., Haifa Bay (IL)

(72) Inventors: Simon Cherniak, Haifa (IL); Rosa Cyjon, Haifa (IL); Ilana Ozer, Yokneam (IL); Igor Nudelman, Haifa (IL)

(73) Assignee: Taro Pharmaceutical Industries Ltd., Haifa Bay, IL (US)

( * ) Notice: Subject to any disclaimer, the term of this patent is extended or adjusted under 35 U.S.C. 154(b) by 0 days.

(21) Appl. No.: 15/402,028

(22) Filed: Jan. 9, 2017

(65) Prior Publication Data

US 2017/0114088 A1   Apr. 27, 2017

Related U.S. Application Data

(63) Continuation of application No. 13/811,141, filed as application No. PCT/IL2011/000580 on Jul. 20, 2011, now abandoned.

(60) Provisional application No. 61/365,950, filed on Jul. 20, 2010.

(51) Int. Cl.
| | | |
|---|---|---|
| C07J 5/00 | (2006.01) | |
| C07J 7/00 | (2006.01) | |
| C07J 75/00 | (2006.01) | |
| C07J 71/00 | (2006.01) | |

(52) U.S. Cl.
CPC ............. *C07J 7/009* (2013.01); *C07J 5/0023* (2013.01); *C07J 5/0038* (2013.01); *C07J 5/0076* (2013.01); *C07J 7/008* (2013.01); *C07J 71/0015* (2013.01); *C07J 75/00* (2013.01); *H05K 999/99* (2013.01)

(58) Field of Classification Search
CPC . C07J 75/00; C07J 5/0023; C07J 7/009; C07J 7/008; C07J 71/0015; C07J 5/0038; C07J 5/0076
USPC ....................................................... 552/588
See application file for complete search history.

(56) References Cited

U.S. PATENT DOCUMENTS

| | | | | |
|---|---|---|---|---|
| 4,255,331 | A | 3/1981 | MacDonald | 260/239.55 |
| 4,990,612 | A | 2/1991 | VanRheenen et al. | 540/89 |
| 4,996,318 | A | 2/1991 | Gall et al. | 544/295 |
| 5,824,670 | A | 10/1998 | Stache et al. | 514/177 |
| 7,098,328 | B2 | 8/2006 | Chernyak et al. | 540/88 |
| 7,718,793 | B2 | 5/2010 | Chernyak et al. | 540/88 |
| 2008/0279928 | A1 | 11/2008 | Moschwitzer | 424/455 |

FOREIGN PATENT DOCUMENTS

GB    1068058    5/1967 ........... C07C 169/36

OTHER PUBLICATIONS

Numazawa et al., "Synthetic Transformations using Iodotrimethylsilane: Regiospecific Deoxygenation of the Dihydroxyacetone Moiety at C-17 of Corticoid Steroids," *Journal of the Chemical Society, Chemical Communications*, 1984(1):(1984).
Numazawa et al., "Regiospecific Deoxygenation of the Dihydroxyacetone Moiety at C-17 of Corticoid Steroids with Iodotrimethylsilane," *Chemical & Pharmaceutical Bulletin*, 34(9):3722-3726 (1986).
Kieslich et al., "Darstellung von 6α-Fluor-16α-methyl-11β.21-dihydroxy-1.4-pregnadien-3.20-dion (Fluocortolon) uber eine Substrat-Struktur-gelenkte spezifische 11β-Hydroxylierung mit *Curvularia lunata,*" *Justus Liebigs Annalen Der Chemie*, 726(1):168-176(1969).
Ho, "Hydrodehalogenation of α-haloketones with iodotrimethylsilane," *Synthetic Communications*, 11(2):101-103 (1981).
Sako et al., "Reductive Cleavage of Heteroaryl C-Halogen Bonds by Iodotrimethylsilane. Facile and Regioselective Dechlorination of Antibiotic Pyrrolnitrin," *J. Org. Chem.*, 66(10):3610-3612 (2001).
Olah et al., "Synthetic Methods and Reactions. 103. Preparation of Alkyl Iodides from Alkyl Fluorides and Chlorides with Iodotrimethylsilane or Its in Situ Analogues," *Journal of Organic Chemistry*, 46:3727-3728 (1981).
Extended European Search Report for European Patent Appl. No. 11809373.1, dated Jun. 26, 2014.
Co-pending PCT Application No. PCT/IL2011/000580 filed Jul. 20, 2011.
International Search Report and Written Opinion for International Application No. PCT/IL2011/000580, issued by PCT dated Dec. 12, 2011.
International Preliminary Report on Patentability for International Application No. PCT/IL2011/000580, issued by PCT dated Jan. 31, 2013.
Co-pending U.S. Appl. No. 13/811,141, filed Mar. 28, 2013.
Office Action for U.S. Appl. No. 13/811,141, issued by USPTO dated Apr. 20, 2015.
Office Action for U.S. Appl. No. 13/811,141, issued by USPTO dated Nov. 12, 2015.
Office Action for U.S. Appl. No. 13/811,141, issued by USPTO dated Feb. 25, 2016.
Office Action for U.S. Appl. No. 13/811,141, issued by USPTO dated Jul. 11, 2016.

*Primary Examiner* — Barbara P Badio

(57) ABSTRACT

The present invention provides an improved process for the preparation of 17-desoxy corticosteroid derivatives in a single chemical step by reacting the 17-hydroxy starting material with an excess of Trimethylsilyl Iodide. The present invention is specifically advantageous in preparing 17-desoxy corticosteroid derivatives having one or more halogen groups at positions 2, 6, 7 or 9 of the corticosteroid such as Clocortolone of Desoximetasone.

33 Claims, No Drawings

US 10,112,970 B2

PROCESS FOR THE PREPARATION OF 17-DESOXY-CORTICOSTEROIDS

CROSS REFERENCE TO RELATED APPLICATIONS

The present application is a continuation of U.S. application Ser. No. 13/811,141 filed Mar. 28, 2013, filed under 35 U.S.C. § 371 as the U.S. national phase of International Application No. PCT/IL2011/000580 filed Jul. 20, 2011, which claims the benefit of priority to U.S. Provisional Application No. 61/365,950 filed Jul. 20, 2010, each of is hereby incorporated in its

FIELD OF THE INVENTION

The present invention is directed to a novel process for the preparation of 17-desoxy-corticosteroids.

BACKGROUND OF THE INVENTION

The corticosteroids are a particular type of steroids having the basic carbon skeletal formula which contains 21 carbon atoms in 4 rings, A thru D.

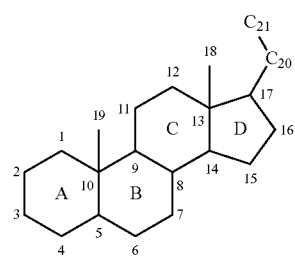

Corticosteroids are known to have anti-inflammatory and immunomodulatory properties useful in the treatment of numerous diseases, including autoimmune and inflammatory diseases.

A large number of 21-hydroxy-20-oxo-17-desoxy-pregnane compounds are known as therapeutically valuable substances with the action of natural corticoids, i.e. of adrenocortical hormones, or they can be used as intermediates for obtaining such active substances. These compounds have principally been obtained by removing the hydroxyl group in carbon 17. The removal of the hydroxyl group is normally carried out in several steps, usually by a direct or indirect exchange of the hydroxyl group for an hydrogen atom. Numazawa et al. (J. Chem. Soc. Chem. Commun., 1984 and Chem. Pharm. Bull., v. 34(9), pp. 3722-3726 (1986)) disclose the deoxygenation of the Dihydroxyacetone moiety at C-17 by using Iodotrimethylsilane for the preparation of Hydrocortisone, Cortisone, Prednisolone and Prednisone. German Patent NOS. 1169444 and 1211194 disclose a multistep synthesis of 17-Desoxicorticosteroids.

The processes described above suffer from various disadvantages. Therefore, there is an unmet need for an improved process for the preparation of 17-desoxy-corticosteroids in a single chemical step from commercially available starting materials.

SUMMARY OF THE INVENTION

The present invention provides an improved process for the preparation of 17-desoxy corticosteroid derivatives in a single chemical step. The present invention is specifically advantageous in preparing 17-desoxy corticosteroid derivatives having one or more halogen groups at positions 2, 6, 7 and 9 of the corticosteroid. In a preferred embodiment, the present invention provides an improved process for the preparation of Diflucortolone, Desoximetasone, Clocortolone, Fluocortolone, 7α-Chloro-11β,21-dihydroxy-16α-methylpregna-1,4-diene-3,20-dione and 2-Bromo-6β,9-difluoro-11,21-dihydroxypregna-1,4-diene-3,20-dione. It was surprisingly found that the process of the present invention provides high region-selectivity of hydroxyl removal at position 17 of the corticosteroid while one or more halogen groups at positions 2, 6, 7 and 9 remain intact. The region-selectivity of the process enables the use of this process for facile preparation of biologically active 17-desoxy corticosteroids having one or more halogen groups at positions 2, 6, 7 and 9.

In one embodiment, the present invention relates to the preparation of a corticosteroid derivative having the general Formula I:

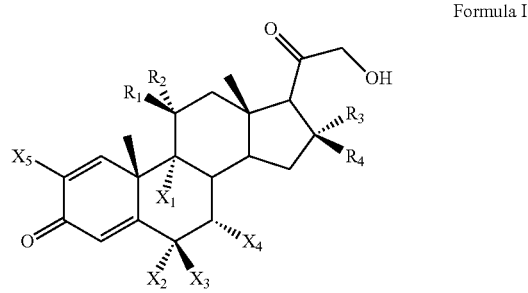

wherein $R_1$ is OH and $R_2$ is H, or $R_1$ and $R_2$ form together a double bond with O, $R_3$ is H and $R_4$ is $CH_3$, or $R_3$ is $CH_3$ and $R_4$ is H, and wherein at least one of $X_{1-5}$ is independently Cl, Br or F.

The preparation process of the present invention comprises reacting the corticosteroid derivative of general Formula II

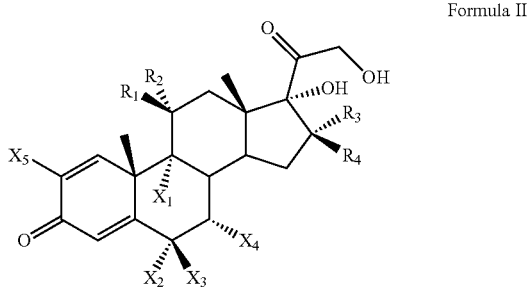

wherein $R_1$-$R_4$ and $X_1$—$X_5$ are as defined above with an excess of Trimethylsilyl Iodide in the presence of an aprotic solvent to yield the 17-desoxy corticosteroid derivative of Formula I.

The process of the present invention does not have the drawback referred to the known processes since it provides 17-desoxy corticosteroid derivatives in a single chemical step. The process of the present invention does not require the protection of the halogen groups which are present in the starting material against undesired reactions with the Trimethylsilyl Iodide reagent. The process of the present invention employs easy to handle reagents and the reaction proceeds with high yield of the 17-desoxy corticosteroid derivative. Particular halogen groups which are present in the starting material are fluorine, bromine or chlorine atoms in one or more of positions 2, 6, 7 and 9 of the corticosteroid.

DETAILED DESCRIPTION OP THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The term "17-desoxy corticosteroid derivatives" as used herein, refers to corticosteroid derivatives having no hydroxyl group in the 17 position and having at least one halogen group at position 2, 6, 7 or 9 of the corticosteroid.

It has surprisingly been found that it is possible to prepare 17-desoxy corticosteroid derivatives having at least one halogen group at position 2, 6, 7 or 9 of the corticosteroid in a single chemical step by reacting the 17-hydroxy starting material with an excess of Trimethylsilyl Iodide. The process of the present invention does not require the protection of the halogen groups present in the starting material against undesired reactions with the Trimethylsilyl Iodide reagent.

The preparation of 17-desoxy corticosteroid derivatives involves reacting the stalling material of Formula II with an excess of Trimethylsilyl Iodide in the presence of an aprotic solvent. The molar ratio between Trimethylsilyl Iodide and the 17-hydroxy starting material is between about 2:1 to about 10:1, preferably between about 2:1 to about 6:1.

The aprotic solvent suitable for the reaction may be for example Acetonitrile, chlorinated solvents, or aromatic solvents, and is preferably methylene chloride or acetonitrile or a combination thereof. Minor amounts of a polar protic co-solvent such as water or $C_1$-$C_4$-alcohol may be added to the reaction in order to enhance the reaction yield. In a preferred embodiment, between about 0.05% to about 1.0% (v/v) of the polar protic co-solvent may be added to the reaction, more preferably, between about 0.1% to about 0.5% (v/v) of the polar protic co-solvent may be added to the reaction. A preferred polar protic co-solvent which may be used is methanol or isopropyl alcohol.

The 17-hydroxy starting materials of Formula II are known compounds which may be obtained commercially. These include for example Flumetasone, Dexametasone, Paramethasone, Betamethasone, 9-Chloro-6α-fluoro-11,17,21-trihydroxy-16α-methylpregna-1,4-diene-3,20-dione, Halopredone or Alclometasone.

The reaction temperature employed for the reaction between Trimethylsilyl Iodide and the 17-hydroxy starting material is in the range from between about −30° C. and about +30° C., more preferably in the range of between about −20° C. and about +20° C.

Depending on the respective conditions (temperature, concentration of Trimethylsilyl Iodide and the starting material, the solvent etc.), the reaction time is from about 15 minutes to about 3 hours, more preferably from about 15 minutes to about 2 hours.

Following the reaction of the 17-hydroxy starting material of Formula II with Trimethylsilyl Iodide, the reaction solution is preferably quenched with sodium thiosulfate or bisulfite. The 17-desoxy product is isolated using one of the common procedures known in the art, preferably using an organic solvent which is not miscible with water such as ethyl acetate or toluene.

Following the extraction, the reaction is completed by washing the organic layer, preferably with a solution of a weak inorganic base such as sodium bicarbonate and a saturated solution of salt such as sodium chloride and evaporating the solution to dryness to yield the 17-desoxy corticosteroid of the invention. In other embodiments, standard chemical procedures for isolation of the corticosteroid may be employed such as extraction or filtration.

The present invention may preferably be used for the preparation of Diflucortolone, Desoximetasone, Clocortolone, Fluocortolone, 7α-Chloro-11β,21-dihydroxy-16α-methylpregna-1,4-diene-3,20-dione and 2-Bromo-6β,9-difluoro-11,21-dihydroxypregna-1,4-diene-3,20-dione. More preferably, the present invention is used for the preparation of Clocortolone and Desoximetasone. In a preferred embodiment, Clocortolone may be further converted to Clocortolone Pivalate by using methods known in the art.

The present invention further relates to a method of preparing Clocortolone having the structure of Formula III,

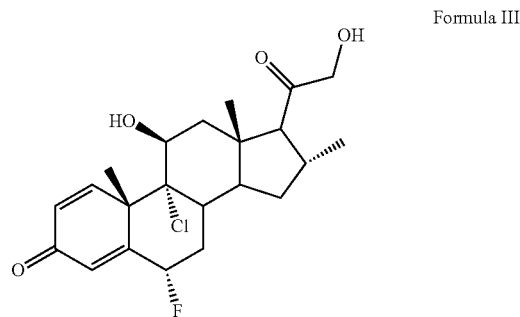

Formula III the method comprising the steps of (a) Reacting a 17-hydroxy epoxide of Formula IV

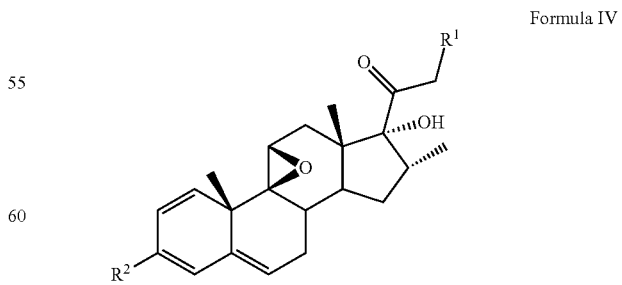

Formula IV with a stereo-selective fluorinating agent to stereo-selectively form a 17-hydroxy epoxide 6α-fluorinated compound of Formula V Formula V

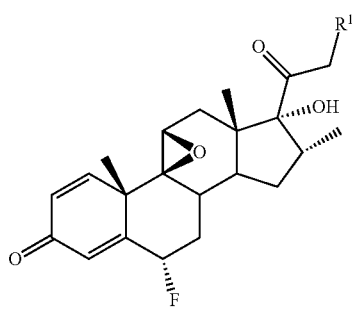

wherein $R^1$ and $R^2$ are OC(O)-Rd; wherein each Rd may be the same or different and is independently selected from $(C_{1-4})$ alkyl, preferably $CH_3$;

(b) hydrolyzing the compound of formula V with an alkaline carbonate, preferably potassium or sodium carbonate in an organic solvent, preferably in $C_1$-$C_3$ alcohol, to form a compound of formula VI;

Formula VI

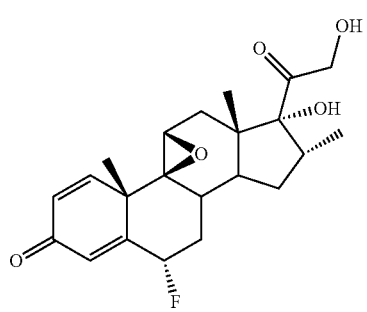

(c) opening the epoxide of the compound of formula VI by a reaction with hydrogen chloride, to form a compound of formula VII;

Formula VII

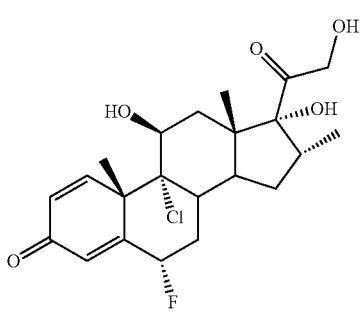

(d) reacting the compound of formula VII with Trimethylsilyl Iodide in the presence of an aprotic solvent, wherein the molar ratio between Trimethylsilyl Iodide and the compound of Formula VII is between about 2:1 to about 10:1, to form a compound of formula III; and
(e) quenching the reaction of step (d) and isolating the compound of Formula III.

The compound of Formula III may be further reacted with Pyvaloyl Chloride in the presence of an organic base, preferably N,N-Dimethylaminopyridine, and an organic solvent, preferably methylene chloride, to form the compound of formula XI.

Formula XI

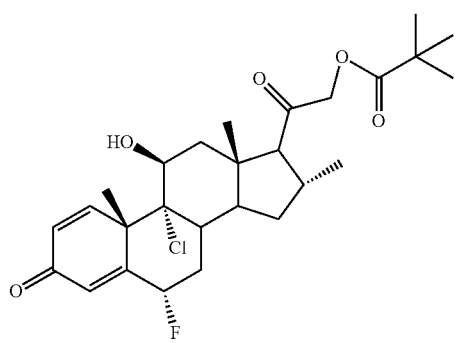

The present invention further relates to a method of preparing Diflucortolone having the structure of Formula XII Formula XII

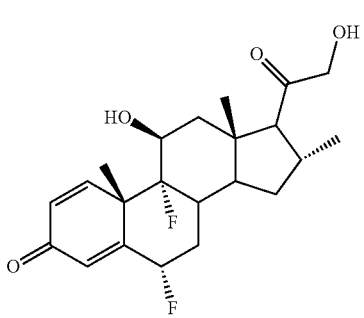

comprising the steps of
a) reacting a 17-hydroxy epoxide of Formula IV

Formula IV

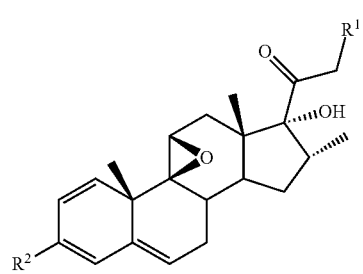

with a stereo-selective fluorinating agent to stereo-selectively form a 17-hydroxy epoxide $6^\alpha$-fluorinated compound of Formula V Formula V

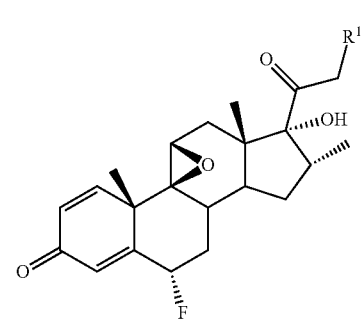

wherein $R^1$ and $R^2$ are OC(O)-Rd; wherein each Rd may be the same or different and is independently selected from $(C_{1-4})$ preferably $CH_3$;

b) hydrolyzing the compound of formula V with an alkaline carbonate, preferably potassium or sodium carbonate in an organic solvent, preferably in $C_1$-$C_3$ alcohol, to form a compound of formula VI;

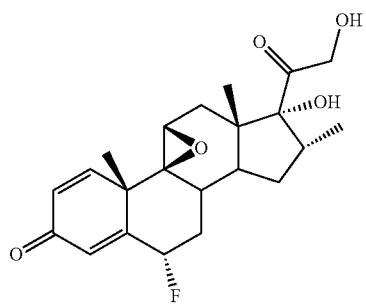

Formula VI c) opening the epoxide of the compound of formula VI by a reaction with hydrogen fluoride to form a compound of formula XIII;

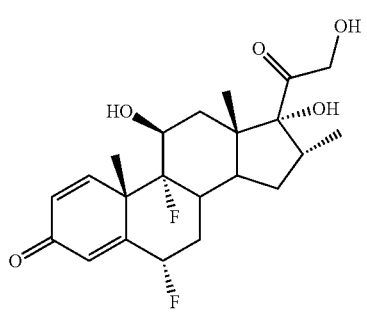

Formula XIII d) reacting the compound of formula XIII with Trimethylsilyl Iodide in the presence of an aprotic solvent, wherein the molar ratio between Trimethylsilyl Iodide and the compound of formula XIII is between about 2:1 to about 10:1, to form a compound of formula XII; and e) quenching the reaction of step (d) and isolating the compound of Formula XII.

The 6α-fluorination method used in the present invention is disclosed in U.S. Pat. Nos. 7,098,328 and 7,718,793, which are assigned to the applicant of the present invention, both are incorporated herein by reference. In a specific embodiment, the stereo-selective fluorinating agent to be used in the present invention is selected from fluoropyridinium compounds and fluoroquinuclidium compounds. In a preferred embodiment, the stereo-selective fluorinating agent is selected from the group consisting of 1-fluoropyridinium triflate, 1-fluoropyridinium tetrafluoroborate, and 1-fluoropyridinium pyridine heptafluorodiborate. Most preferred fluorinating agent is SELECTFLUOR®, 1-chloromethyl-4-fluoro-1,4-diazoniabicyclo[2.2.2]octane bis-(tetrafluoroborate).

The 17-hydroxy epoxide of Formula IV is preferably generated by reacting a compound having the formula VIII

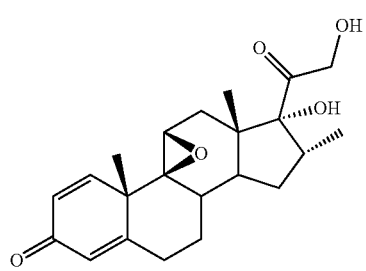

Formula VIII with an acetylating agent in the presence of a weak base and a polar solvent to form the compound of formula IX; and

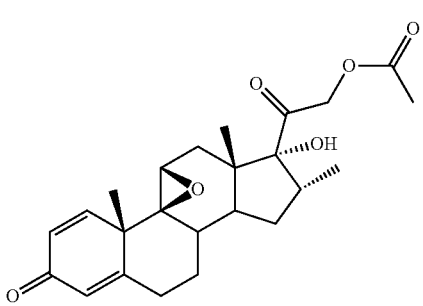

Formula IX reacting the compound of formula IX with isopropenyl acetate to form the compound of Formula X.

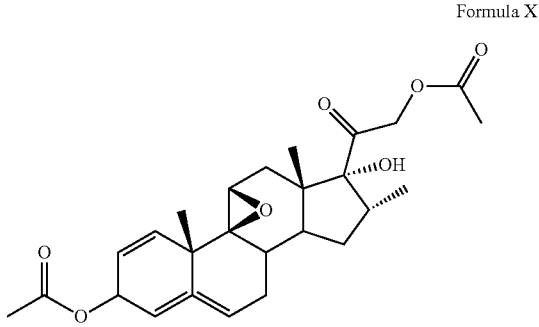

Formula X

The acetylating agent is preferably acetic anhydride or acetyl chloride, the weak base is preferably sodium acetate or potassium acetate and the polar solvent is preferably dimethylacetamide or dimethylformamide.

The reaction of step (a) is conducted in the presence of a solvent selected from the group consisting of acetonitrile and dichloromethane, preferably with acetonitrile. The reaction is preferably conducted at room temperature.

The present invention also relates to medicinal preparations in the form of dosage units that contain at least one of the 17-desoxy corticosteroid derivative according to the invention alone or in admixture with one or more adjuncts, especially medicinal preparations in solid or semi-solid form.

The following examples are presented in order to more fully illustrate the preferred embodiments of the invention. They should in no way be construed, however, as limiting the broad scope of the invention.

EXAMPLES

Methods:

The structures of the 17-desoxy corticosteroid derivatives produced by the process of the present invention were confirmed by Infra Red spectra, MS spectra and NMR methods and by comparison with the corresponding standards.

$^1$H- and $^{13}$C NMR spectra were determined on a Varian 500 MHz using suitable deuterated DMSO and Tetramethylsilane (TMS) as an internal reference. The chemical shifts were expressed in ppm (δ) downfield from TMS and coupling constant (J) in Hz. Known standard NMR techniques were used to determine multiplicity which was abbreviated as follows: s—singlet, d—doublet, t—triplet, q—quartet, m—multiplet, dd—double doublet.

Mass spectra were taken on a Finnigan LC/MS model LCQ DUO spectrometer using Cl. Data were expressed in m/e units and with relative intensities given in percentage (%).

IR spectra were recorded on Nicolet Avatar 360 FT-IR instrument using potassium bromide pellets. The absorption wavelength is expressed in cm$^{-1}$.

Example 1

Synthesis of Diflucotolone from Flumetasone 20 ml of dry Acetonitrile cooled to −20° C. and 0.7 ml of Trimethylsilyl Iodide were added to 1.0 g (2.43 mmol) of Flumetasone (Formula II: $R_1$ is OH, $R_3$ is $CH_3$, $X_1$ and $X_2$ are F, all other R and X are H) in the stream of dry Nitrogen. The reaction mixture was stirred for 2 hours at −20° C., quenched with 5% sodium thiosulfate and extracted with Ethyl Acetate. The organic layer was washed with a solution of sodium bicarbonate and a saturated solution of sodium chloride and evaporated to dryness. 0.9 g (93% yield relative to the starting material) of Diflucortolone was obtained (Formula I: $R_1$ is OH, $R_3$ is $CH_3$, $X_1$ and $X_2$ are F, all other R and X are H).

MS, IR and NMR results of the Diflucortolone product are as following:

MS: 395 (MH+), 375 (MH-HF), 355 (MH-2HF).

IR: IR (KBr): 3440 (OH), 1720 (CO), 1671 (CO), 1627 (C=C), 1605 (C=).

$^1$H-NMR: 7.29 (d, 1H, H-1), 6.28 (dd, 1H, H-2), 5.68 (m, 0.5H, H-6), 5.61 (m, 0.5H, H-6), 5.51 (m, 1H, HO-11), 5.03 (t, 1H, HO-21), 4.11 (m, 1H, H-11), 4.01 (d, 2H, H-21), 2.54-2.68 (m, 1H), 2.39-2.50 (m, 1H), 2.19-2.25 (m, 2H), 1.88 (d, 1H), 1.62-1.76 (m, 3H), 1.48 (s, 3H, Me-19), 1.42-1.56 (m, 1H), 1.21-1.1.16 (m, 2H), 0.872 (d, 3H, Me-22), 0.83 (s, 3H, Me-18).

$^{13}$C-NMR: 209.714 ($C_{20}$), 184.393 ($C_3$), 162.910, 162.808 ($C_5$, F-splitting), 151.952 ($C_1$), 128.952 ($C_2$), 119.483, 119.375 ($C_4$, F-splitting), 100.768, 99.360 ($C_9$, F-splitting), 87.915, 86.081 ($C_6$, F-splitting), 70.080, 69.796 ($C_{11}$, F-splitting), 69.010 ($C_{21}$), 66.784 ($C_{17}$), 59.683 ($C_{13}$), 48.116, 47.940, 47.906, 47.717 ($C_{10}$, F-splitting), 44.481 ($C_{13}$), 42.667 ($C_{14}$), 33.753, 33.598 ($C_7$, F-splitting), 32.548 ($C_{15}$), 32.061, 31.973, 31.912, 31.824 (C8, F-splitting), 30.146 ($C_{12}$), 22.727, 22.680 (C19, F-splitting), 21.604 (C22), 15.722 (C18).

Example 2

Synthesis of Desoximetasone from Dexametasone

Desoximetasone (Formula I: $R_1$ is OH, $R_3$ is $Ch_3$, $X_1$ is F, all other R and X are H) was obtained from Dexametasone (Formula II: $R_1$=is OH, $R_3$ is $CH_3$, $X_1$ is F, all other R and X are H) by reacting Dexametasone with Trimethylsilyl Iodide in Acetonitrile as described in Example 1, except that the reaction mixture was stirred for 30 min at 0° C. The yield relative to the starting material was 80%.

MS and IR results of the Desoximetasone product are as following:

MS: 377 (MH+), 357 (MH-HF), 339 (MH-HF—$H_2O$).

IR (KBr): 3517 (OH), 3348 (OH), 1720 (CO), 1671 (CO), 1616 (C=C), 1599 (C=C).

Example 3

Synthesis of Desoximetasone from Dexametasone 15 g (38.22 mmol) of Dexamethasone were dissolved in 225 ml of a mixture of Dichloromethane and Acetonitrile (95:5) cooled to −8° C. and 16.5 ml of Trimethylsilyl iodide were added. The reaction mixture was stirred for 1 hour at −8° C., and quenched with 30% sodium bisulfite. The Dichloromethane solution was washed with a solution of sodium bicarbonate. A solution of 115 ml of Hydrochloric acid (32%) was added to the Dichloromethane solution and the mixture was stirred for 1 hour. The Dichloromethane solution was washed with 110 ml of Hydrochloric acid (32%). The Hydrochloric acid solution (225 ml) was then diluted with 200 ml of water, stirred for 1 hour and filtered, followed by the addition of another 250 ml of water to the solution. After 1 hour the mixture was filtered to give 12 g of Desoximetasone (83%).

Example 4

Synthesis of Clocortolone from 9-Chloro-6α-fluoro-11,17,21-trihydroxy-16α-methylpregna-1,4-diene-3,20-dione Clocortolone (Formula I: $R_1$ is OH, $R_3$ is $CH_3$, $X_1$ is Cl, $X_2$ is F, all other R and X are H) was obtained from 9-Chloro-6α-fluoro-11,17,21-trihydroxy-16α-methyl-pregna-1,4-diene-3,20-dione (Formula II: $R_1$ is OH, $R_3$ is $CH_3$, $X_1$ is Cl, $X_2$ is F, all other R and X are H) by reacting with Trimethylsilyl Iodide in Acetonitrile as described in Example 1, except that the reaction mixture was stirred for 15 minutes at 20° C. The yield relative to the starting material was 63%.

MS, IR and NMR results of the Clocortolone product are as following:

MS: 411 (MH+), 391 (MH—HF), 371 (MH-2HF), 353 (MH-2HF—$H_2O$).

IR (KBr): 3583 (OH), 3506 (OH), 3303 (OH), 1704 (CO), 1761 (CO), 1632 (C=C), 1600 (C=C).

$^1$H-NMR: 7.30 (d, H, H-1), 6.27 (dd, 1H, H-2), 5.09 (m, 1.5H, H-6, OH-11), 5.55 (m, 0.5H, H-6), 5.04 (t, 1H, HO-21), 4.30 (m, 1H, H-11), 4.02 (d, 2H, H-21), 2.54-2.68 (m, 1H), 2.39-2.50 (m, 1H), 2.19-2.25 (m, 2H), 1.88 (d, 1H), 1.62-1.76 (m, 3H), 1.59 (s, 3H, Me-19), 1.18-1.25 (m, 2H), 0.872 (d, 3H, Me-22), 0.89 (s, 3H, Me-18).

$^{13}$C-NMR: 209.707 ($C_{20}$), 184.414 ($C_3$), 162.673, 162.565 ($C_5$, F-splitting), 152.080 ($C_1$), 128.607 ($C_2$), 119.422, 119.375 ($C_4$, F-splitting), 87.414 ($C_9$, F-splitting), 85.979, 84.341 ($C_6$, F-splitting), 73.451 ($C_{11}$), 69.017 ($C_{21}$), 66.851 ($C_{17}$), 59.683 ($C_{13}$) 49.903, 47.805 ($C_{10}$, F-splitting), 44.421 ($C_{13}$), 42.078 ($C_{14}$), 33.855, 33.699 ($C_7$, F-splitting), 32.609 ($C_{15}$), 32.521, 32.183 ($C_8$, F-splitting), 30.132 ($C_{12}$), 24.135 ($C_{19}$), 21.631 ($C_{22}$), 16.331 ($C_{18}$).

Example 5

Synthesis of Clocortolone from 9-Chloro-6α-fluoro-11,17,21-trihydroxy-16α-methylpregna-1,4-diene-3,20-dione Clocortolone was obtained as described in Example 4 using Acetonitrile that also contained 0.5% (v/v) of water. The yield relative to the starting material was 60%.

Example 6

Synthesis of Clocortolone from 9-Chloro-6α-fluoro-11,17,21-trihydroxy-16α-methylpregna-1,4-diene-3,20-dione 1 g of 9-Chloro-6α-flouro-11,17,21-trihydroxy-16α-methylpregna-1,4-diene-3,20-dione (2.34 mmol) was reacted with 1.2 ml Thimethylsilyl Iodide (8.2 mmol) in 20 ml acetonitrile containing 0.1% methanol at 0° C. for 30 minutes in a stream of dry Nitrogen. The reaction mixture was quenched with 5% sodium thiosulfate and sodium bicarbonate saturated solution. Ethyl acetate was added to the reaction mixture. The product was filtered, washed with water and dried to obtain clocortolone. The yield relative to the starting material was 72%.

Example 7

Synthesis of Clocortolone from 9-Chloro-6α-11,17,21-trihydroxy-16α-methylpregna-1,4,-diene-3,20-dione Clocortolone was obtained as described in Example 4 using Acetonitrile that also contained 0.1% (v/v) of isopropyl alcohol. The yield relative to the starting material was 85%.

Example 8

Synthesis of Fluocortolone from Paramethasone

Fluocortolone (Formula I: $R_1$ is OH, $R_3$ is $CH_3$, $X_2$ is F, all other R and X are H) is obtained by reaction of Paramethasone (Formula II: $R_1$ is OH, $R_3$ is $CH_3$, $X_2$ is F, all other X and R are H) with Trimethylsilyl Iodide in Acetonitrile as described in Example 1.

Example 9

Desoxigenation of Alclometasone

7α-Chloro-11β,21-dihydroxy-16α-methylpregna-1,4-diene-3,20-dione (Formula I: $R_1$ is OH, $R_3$ is $CH_3$, $X_4$ is Cl, all other X and R are H) is obtained from Alclometasone (Formula II: $R_1$ is OH, $R_3$ is $CH_3$, $X_4$ is Cl, all other X and R are H) by reaction of Alclometasone with Trimethylsilyl Iodide in Acetonitrile as described in Example 1.

Example 10

Desoxigenation of Halopredone

2-Bromo-6β,9-difluoro-11,21-dihydroxypregna-1,4-diene-3,20-dione (Formula I: $R_1$ is OH, $X_1$ and $X_3$ are F, $X_5$ is Br, all other X and R are H) is obtained from Halopredone (Formula II: $R_1$ is OH, $X_1$ and $X_3$ are F, $X_5$ is Br, all other X and R are H) by reaction of Halopredone with Trimethylsilyl Iodide in Acetonitrile as described in Example 1.

Example 11

Desoxygenation of Betamethasone

11β,21-Dihydroxy-9-fluoro-16β-methylpregna-1,4-diene-3,20-dione (Formula I: $R_1$ is OH, $R_4$ is $CH_3$, $X_1$ is F, all other X and R are H) is obtained by the reaction of Betamethasone (Formula II: $R_1$ is OH, $R_4$ is $CH_3$, $X_1$ is F, all other X and R are H) with Trimethylsilyl Iodide in Acetonitrile as described in Example 1.

Example 12

Synthesis of Clocortolone Pivalate

Clocortolone was converted into the corresponding Clocortolone Pivalate by the reaction with Pivaloyl Chloride. 9 g (0.022 moles) of Clocortolone were diluted with 90 ml of Methylene Chloride and 13.38 g (0.11 moles) of N,N-Dimethylaminopyridine were added followed by 5.4 ml (0.044 moles) of Pyvaloyl Chloride. The mixture was stirred overnight and washed with diluted Hydrochloric acid and water. The organic solution was separated, dried with sodium sulfate and evaporated to dryness. 8.5 g of Clocortolone Pivalate were obtained. The crude product was purified by crystallization from Methanol-Methylene Chloride mixture.

Example 13

Synthesis of 17,21-Dihydroxy-9β,11β-epoxy-16α-methyl-pregna-1,4-diene-3,20-dione 21-acetate from 17,21-Dihydroxy-9β,11β-epoxy-16α-methyl-pregna-1,4-diene-3,20-dione 100 g of 17,21-dihydroxy-9β,11β-epoxy-16α-methyl-pregna-1,4-diene-3,20-dione dissolved in 500 ml N,N-Dimethylacetamide and 44 g of Potassium Acetate was added followed by the addition of 110 ml of Acetic Anhydride. The reaction mixture was stirred for 2 hours at ambient temperature. 1000 ml of water was added and the suspension formed was filtered. The precipitate was washed with water and dried in vacuum. 109.7 g (98%) of 17-hydroxy-9β,11β-epoxy-16α-methyl-pregna-1,4-diene-3,20-dione 21-acetate was obtained.

Example 14

Synthesis of 6α-fluoro-17,21-hydroxy-9β,11β-epoxy-16α-methylpregna-1,4-diene-3,20-dione 21-acetate from 17-hydroxy-9β,11β-epoxy-16α-methyl-pregna-1,4-diene-3,20 dione 21-acetate 100 g 17-hydroxy-9β,11β-epoxy-16α-methyl-pregna-1,4-diene-3,20-dione 21-acetate was dissolved in Isopropenyl Acetate (1050 ml) and 2 ml of concentrated Sulfuric acid was added to formed a suspension. The mixture was stirred for half an hour and the reaction was quenched by the addition of Triethylamine to obtain neutral pH. The formed solution was evaporated to dryness, the residue was dissolved in acetonitrile (1000 ml) and 137 g F-TEDA was added. The mixture was stirred overnight, diluted with water and filtered. The precipitate was washed with water, triturated with methanol and filtered. 60 g 6α-fluoro-17,21- dihydroxy-9β,11β-epoxy-16α-methylpregna-1,4-diene-3,20-dione 21-acetate was obtained.

Example 15

Synthesis of 6α-17,21-dihydroxy-9β,11β-epoxy-16α-methylpregna-1,4-diene-3,20-dione from 6α-fluoro-17,21-dihydroxy-9β,11β-epoxy-16-α-methylpregna-1,4-diene-3,20-dione 21-acetate A solution of potassium carbonate (45 g) in water (280 ml) was added to a suspension of 47 g of 6α-fluoro-17,21-dihydroxy-9β,11β-epoxy-16-α-methylpregna-1,4-diene-3,20-dione 21-acetate in methanol (565 ml). The reaction mixture was stirred for 10 hrs and diluted with water. A precipitate of 6α-fluoro-17,21-dihydroxy-9β,11β-epoxy-16α-methylpregna-1,4-diene-3,20-dione was formed. The product was filtered, washed with water and dried. The Yield was 36 g.

Example 16

Synthesis of Diflucortolone from 6α-fluoro-17,21-dihydroxy-9⊕,11β-epoxy-16α-methylpregna-1,4-diene-3,20-dione A solution of 6α-fluoro-17,21-dihydroxy-9β,11β-epoxy-16α-methylpregna-1,4-diene-3,20-dione (2.4 g) in 70% hydrofluoric acid (25 ml) was stirred for 5 hours at –10° C. to –15° C. The solution was then diluted with 250 ml of water, stirred for 1 more hour and the precipitate of Flumethasone was filtered.

20 ml of dry Acetonitrile cooled to –20° C. and 0.7 ml of Trimethylsilyl Iodide were added to 1.0 g (2.43 mmol) of Flumethasone in the stream of dry Nitrogen. The reaction mixture was stirred for 2 hours at –20° C., quenched with 5% sodium thiosulfate and extracted with Ethyl Acetate. The organic layer was washed with a solution of sodium bicarbonate and a saturated solution of sodium chloride followed by evaporation to dryness to obtain 0.9 (93%) g of Diflucortolone.

Example 17

Synthesis of Clocortolone Pivalate from 6α-fluoro-17,21-dihydroxy-9β,11β-epoxy-16α-methylpregna-1,4-diene-3,20-dione A solution of 6α-fluoro-17,21-dihydroxy-9β,11β-methylpregna-1,4-diene-3,20-dione (2.4 g) in 70% hydrochloric acid (25 ml) was stirred for 5 hours at –10° C. to –15° C. The solution was then diluted with 250 ml of water, stirred for 1 more hour and the precipitate of 9-Chloro-6α-fluoro-11,17,21-trihydroxy-16α-methylpregna-1,4-diene-3,20-dione was filtered.

Clocortolone was obtained from 9-Chloro-6α-fluoro-11,17,21-trihydroxy-16α-methylpregna-1,4-diene-3,20-dione by reacting with Trimethylsilyl Iodide in Acetonitrile as described in Example 16, except that the reaction mixture was stirred for 15 minutes at 20° C. The yield relative to the starting material was 63%.

To obtain Clocortolone Pivalate, 9 g (0.22 moles) of Clocortolone were dissolved in 90 ml of Methylene Chloride and 13.37 g (0.11 moles) of N,N-Dimethylaminopyridine were added followed by 5.4 ml (0.044 moles) of Pyvaloyl Chloride. The mixture was stirred overnight and washed with diluted Hydrochloric acid and water. The organic solution was separated, dried with sodium sulfate and evaporated to dryness. 8.5 g of Clocortolone Pivalate were obtained. The crude product was purified by crystallization from Methanol-Methylene Chloride mixture.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:
1. A process for preparing a compound of Formula I

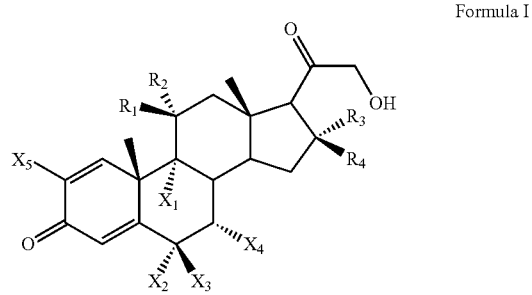

Formula I in which $R_1$ is OH and $R_2$ is H, or $R_1$ and $R_2$ form together a double bond with O, $R_3$ is H and $R_4$ is $CH_3$, or $R_3$ is $CH_3$ and $R_4$ is H, and wherein at least one of $X_{1-5}$ is independently Cl, Br or F, and all other of $X_{1-5}$ are H, comprising the steps of:
(a) reacting a compound of formula II

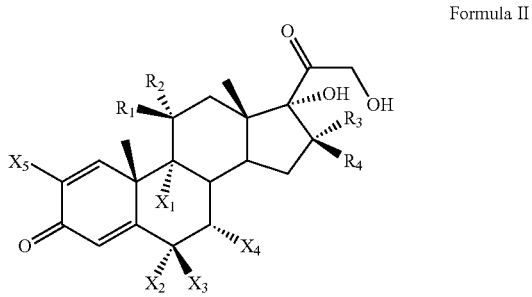

Formula II in which $R_1$-$R_4$ and $X_{1-5}$ are as defined in Formula I with Trimethylsilyl Iodide in a solution of an aprotic solvent, wherein the molar ratio between Trimethylsilyl Iodide and the compound of Formula II is about 2:1 to about 10:1;
(b) quenching the reaction of step (a);
(c) extracting the compound of Formula I from the solution of step (b) using an organic solvent to yield an organic layer comprising the compound of Formula I; and
(d) isolating the compound of Formula I from the organic layer of step (c).

2. The process of claim 1, wherein the aprotic solvent of step (a) is methylene chloride or acetonitrile or a combination thereof.

3. The process of claim 1, wherein the compound of formula II is selected from Flumetasone, Dexametasone, Paramethasone, 9-Chloro-6α-fluoro-11,17,21-trihydroxy-16α-methylpregna-1,4-diene-3,20-dione, Halopredone and Alclometasone.

4. The process of claim 1, wherein the molar ratio between Trimethylsilyl Iodide and the compound of Formula II is about 2:1 to about 6:1.

5. The process of claim 1, wherein the reaction temperature employed in step (a) is in the range from about −30° C. and about +30° C.

6. The process of claim 1, wherein the compound of Formula I is selected from Diflucortolone, Desoximetasone, Clocortolone, Fluocortolone, 7α-Chloro-11β,21-dihydroxy-16α-methylpregna-1,4-diene-3,20-dione and 2-Bromo-6β,9-difluoro-11,21-dihydroxypregna-1,4-diene-3,20-dione.

7. The process of claim 1, wherein the quenching of step (b) is performed by adding to the reaction solution of step (a) a solution of sodium thiosulfate or bisulfate.

8. The process of claim 1, wherein the first organic solvent of step (c) is selected from ethyl acetate and toluene.

9. The process of claim 1, wherein the isolation of the compound of Formula I in step (d) is performed by evaporation or filtration.

10. The process of claim 1, wherein the solution of step (a) further comprises about 0.05% to about 0.5% (v/v) of a polar protic co-solvent.

11. The process of claim 10, wherein the polar protic co-solvent is selected from water and $C_1$-$C_4$-alcohol.

12. The process of claim 1, the compound of Formula I in which $R_1$ is OH, $R_4$ is $CH_3$, $X_1$ is Cl and $X_2$ is F.

13. The process of claim 1, the compound of Formula I in which $R_1$ is OH, $R_4$ is $CH_3$ and $X_1$ is F.

14. A method of preparing Clocortolone of Formula III

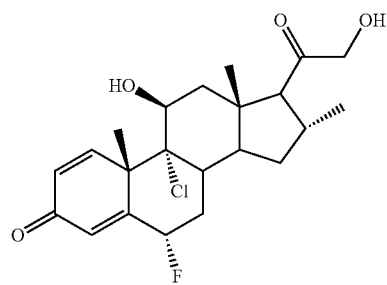

Formula III comprising the steps of:
a) reacting a 17-hydroxy epoxide of Formula IV

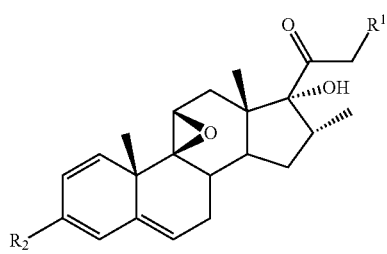

Formula IV with a stereo-selective fluorinating agent to stereo-selectively form a 17-hydroxy epoxide 6α-fluorinated compound of Formula V

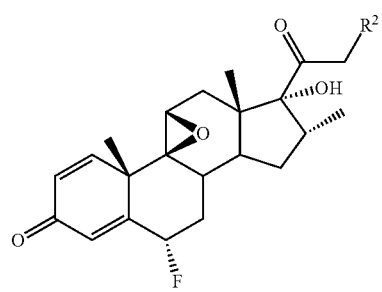

Formula V wherein $R^1$ and $R^2$ are OC(O)—Rd, each of Rd may be the same or different and is independently selected from $(C_{1-4})$ alkyl;
b) hydrolyzing the compound of formula V with an alkaline carbonate in a first organic solvent to form a compound of formula VI;

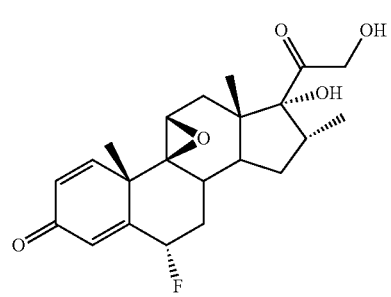

Formula VI c) opening the epoxide of the compound of formula VI by a reaction with hydrogen chloride to form a compound of formula VII;

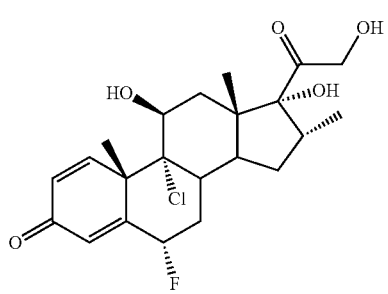

Formula VII d) reacting the compound of formula VII with Trimethylsilyl Iodide in a solution of an aprotic solvent, wherein the molar ratio between Trimethylsilyl Iodide and the compound of Formula VII is about 2:1 to about 10:1, to form a compound of formula III; and
e) quenching the reaction of step (d) and isolating the compound of Formula III.

15. The method of claim 14, wherein the $(C_{1-4})$ alkyl is $CH_3$.

16. The method of claim 14, wherein the stereo-selective fluorinating agent of step (a) is selected from fluoropyridinium compounds and fluoroquinuclidium compounds.

17. The method of claim 16, wherein the stereo-selective fluorinating agent is selected from the group consisting of 1-fluoropyridinium triflate, 1-fluoropyridinium tetrafluoroborate, and 1-fluoropyridinium pyridine heptafluorodiborate.

18. The method of claim 17, wherein the stereo-selective fluorinating agent is 1-chloromethyl-4-fluoro-1,4-diazoniabicyclol[2.2.2]octane bis-(tetrafluoroborate).

19. The method of claim 15, the 21-ester 17-hydroxy epoxide of Formula IV is generated by (a) reacting a compound having the formula VIII

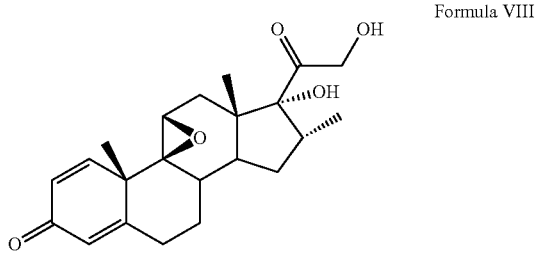 [SMILES: C[C@@H]1CC2C3CCC4=CC(=O)C=C[C@]4(C)[C@@]34O[C@H]4C[C@]2(C)[C@@]1(O)C(=O)CO]

Formula VIII with an acetylating agent in the presence of a weak base and a polar solvent to form the compound of formula IX;

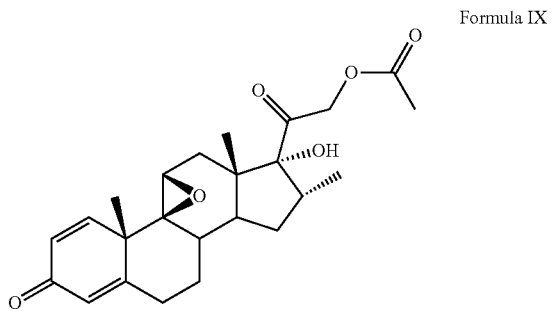 [SMILES: CC(=O)OCC(=O)[C@@]1(O)[C@H](C)CC2C3CCC4=CC(=O)C=C[C@]4(C)[C@@]34O[C@H]4C[C@@]21C]

Formula IX and
(b) reacting the compound of formula IX with isopropenyl acetate to form the compound of Formula X, the generated 21-ester 17-hydroxy epoxide of Formula IV

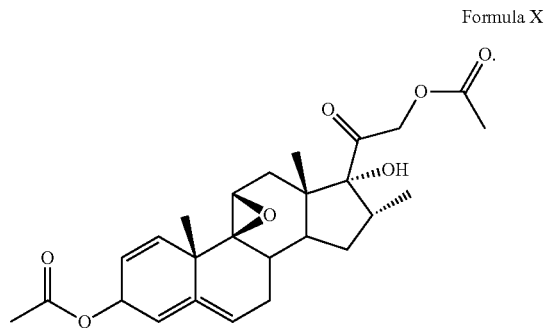

Formula X

20. The method of claim 19, wherein the acetylating agent is acetic anhydride or acetyl chloride, the weak base is sodium acetate or potassium acetate and the polar solvent is dimethylacetamide or dimethylformamide.

21. The method of claim 14, wherein the reaction of step (a) is conducted in the presence of a solvent selected from the group consisting of acetonitrile and dichloromethane.

22. The method of claim 21, wherein the reaction of step (a) is conducted in the presence of acetonitrile.

23. The method of claim 14, wherein the reaction of step (a) is conducted at room temperature.

24. The method of claim 14, wherein the alkaline carbonate of step (b) is potassium or sodium carbonate.

25. The method of claim 14, wherein the first organic solvent of step (b) is a $C_1$-$C_3$ alcohol.

26. The method of claim 14, wherein the aprotic solvent of step (d) is methylene chloride or acetonitrile or a combination thereof.

27. The method of claim 14, wherein the quenching of step (e) is performed by the addition of a solution of sodium thiosulfate or bisulfate to the reaction of step (d).

28. The method of claim 14, wherein the compound of Formula III is extracted from the reaction of step (e) using a second organic solvent to yield an organic layer of the compound of Formula III.

29. The method of claim 28, wherein the second organic solvent is selected from ethyl acetate and toluene.

30. The method of claim 14, wherein the isolation of the compound of Formula III is performed by evaporation or filtration.

31. The method of claim 14, wherein the compound of Formula III is further reacted with Pyvaloyl Chloride in the presence of an organic base and a third organic solvent to form the compound of formula XI Formula XI

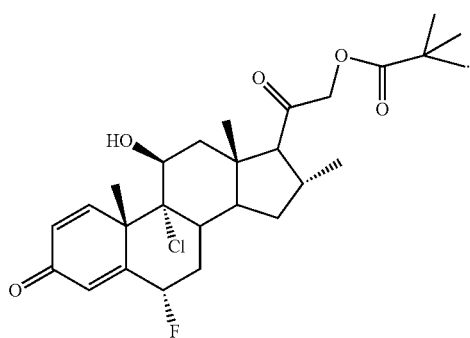

32. The method of claim 31, wherein the organic base is N,N-Dimethylaminopyridine.

33. The method of claim 31, wherein the third organic solvent is methylene chloride.

* * * * *